(12) United States Patent
Maly et al.

(10) Patent No.: US 12,035,928 B2
(45) Date of Patent: Jul. 16, 2024

(54) DEVICES AND METHODS FOR CORRECTION OF HIP DEFORMITIES

(71) Applicant: NextWave Medical, LLC, Poway, CA (US)

(72) Inventors: Richard Maly, San Diego, CA (US); Vidyadhar Upasani, San Diego, CA (US); Yuval Shenkal, San Diego, CA (US)

(73) Assignee: NextWave Medical, LLC, Poway, CA (US)

( * ) Notice: Subject to any disclaimer, the term of this patent is extended or adjusted under 35 U.S.C. 154(b) by 0 days.

(21) Appl. No.: 17/986,759

(22) Filed: Nov. 14, 2022

(65) Prior Publication Data
US 2023/0149030 A1    May 18, 2023

Related U.S. Application Data

(60) Provisional application No. 63/279,006, filed on Nov. 12, 2021.

(51) Int. Cl.
| | | |
|---|---|---|
| *A61B 17/80* | (2006.01) | |
| *A61B 17/16* | (2006.01) | |
| *A61B 17/17* | (2006.01) | |

(52) U.S. Cl.
CPC ...... *A61B 17/1721* (2013.01); *A61B 17/1697* (2013.01); *A61B 17/1742* (2013.01); *A61B 17/809* (2013.01)

(58) Field of Classification Search
CPC .............. A61B 17/809; A61B 17/1721; A61B 17/1697; A61B 17/1742; A61B 17/8061
USPC .................................................. 606/71, 297
See application file for complete search history.

(56) References Cited

U.S. PATENT DOCUMENTS

| | | | | |
|---|---|---|---|---|
| 583,455 | A * | 6/1897 | Bush .................. | A61B 17/8004 606/212 |
| 3,025,853 | A * | 3/1962 | Mason ................ | A61B 17/746 606/301 |
| 3,256,877 | A * | 6/1966 | Haboush ............. | A61B 17/746 606/67 |
| 4,438,762 | A * | 3/1984 | Kyle .................... | A61B 17/746 606/65 |
| 4,936,844 | A * | 6/1990 | Chandler ........... | A61B 17/0642 606/282 |
| 4,978,349 | A * | 12/1990 | Frigg .................. | A61B 17/744 606/62 |
| 5,006,120 | A * | 4/1991 | Carter ................. | A61B 17/809 606/281 |

(Continued)

FOREIGN PATENT DOCUMENTS

| | | |
|---|---|---|
| EP | 0645985 | 4/1995 |
| JP | 2004216056 | 8/2004 |

*Primary Examiner* — David W Bates
(74) *Attorney, Agent, or Firm* — Lewis Kohn & Walker LLP; David M. Kohn

(57) ABSTRACT

An instrument for use in entering bone, comprising a blade having at least two prongs and a center cannulation to accommodate a guide wire, wherein the center-cannulated guide wire allows for precise placement of the instrument within the proximal femoral neck of an individual in the treatment of certain orthopedic conditions, including those related to the surgical correction of specific deformities, particular in children and adolescents, namely, proximal femoral deformities.

9 Claims, 7 Drawing Sheets

(56) References Cited

U.S. PATENT DOCUMENTS

| | | | | |
|---|---|---|---|---|
| 5,190,544 A * | 3/1993 | Chapman | A61B 17/8061 | 606/280 |
| 5,197,966 A * | 3/1993 | Sommerkamp | A61B 17/8061 | 606/280 |
| 5,300,074 A * | 4/1994 | Frigg | A61B 17/725 | 606/70 |
| 5,484,439 A * | 1/1996 | Olson | A61B 17/746 | 606/65 |
| 5,674,222 A * | 10/1997 | Berger | A61B 17/809 | 606/65 |
| 6,183,475 B1 * | 2/2001 | Lester | A61B 17/8095 | 606/65 |
| 7,090,676 B2 * | 8/2006 | Huebner | A61B 17/8033 | 606/71 |
| 7,316,687 B2 * | 1/2008 | Aikins | A61B 17/1668 | 606/86 A |
| 7,666,207 B2 * | 2/2010 | Schlapfer | A61B 17/8625 | 606/246 |
| 8,177,819 B2 * | 5/2012 | Huebner | A61B 17/8061 | 606/281 |
| 8,197,484 B2 * | 6/2012 | Sato | A61B 17/8872 | 606/915 |
| 8,579,898 B2 * | 11/2013 | Prandi | A61B 17/8061 | 606/280 |
| 8,915,918 B2 * | 12/2014 | Graham | A61B 17/8061 | 606/70 |
| 9,131,973 B2 * | 9/2015 | Rollinghoff | A61B 17/88 | |
| 9,662,146 B2 * | 5/2017 | Stern | A61B 17/8872 | |
| 9,763,710 B2 * | 9/2017 | Orsak | A61B 17/742 | |
| 9,956,015 B2 * | 5/2018 | Ehmke | A61B 17/80 | |
| 10,231,768 B2 * | 3/2019 | Grady, Jr. | A61B 17/809 | |
| 2004/0102778 A1 * | 5/2004 | Huebner | A61B 17/1735 | 606/71 |
| 2005/0107795 A1 * | 5/2005 | Morris | A61L 31/005 | 606/283 |
| 2006/0004361 A1 * | 1/2006 | Hayeck | A61B 17/74 | 606/70 |
| 2006/0089648 A1 * | 4/2006 | Masini | A61B 17/1615 | 606/291 |
| 2009/0012569 A1 * | 1/2009 | Dall | A61B 17/8085 | 606/280 |
| 2011/0152864 A1 * | 6/2011 | Ahmadi | A61B 17/1742 | 606/281 |
| 2011/0276097 A1 * | 11/2011 | Raven, III | A61B 17/8061 | 606/284 |
| 2013/0041375 A1 * | 2/2013 | Fierlbeck | A61B 17/809 | 606/281 |
| 2016/0066968 A1 * | 3/2016 | Orsak | A61B 17/74 | 606/281 |
| 2017/0000537 A1 * | 1/2017 | Fallin | A61B 17/808 | |

* cited by examiner

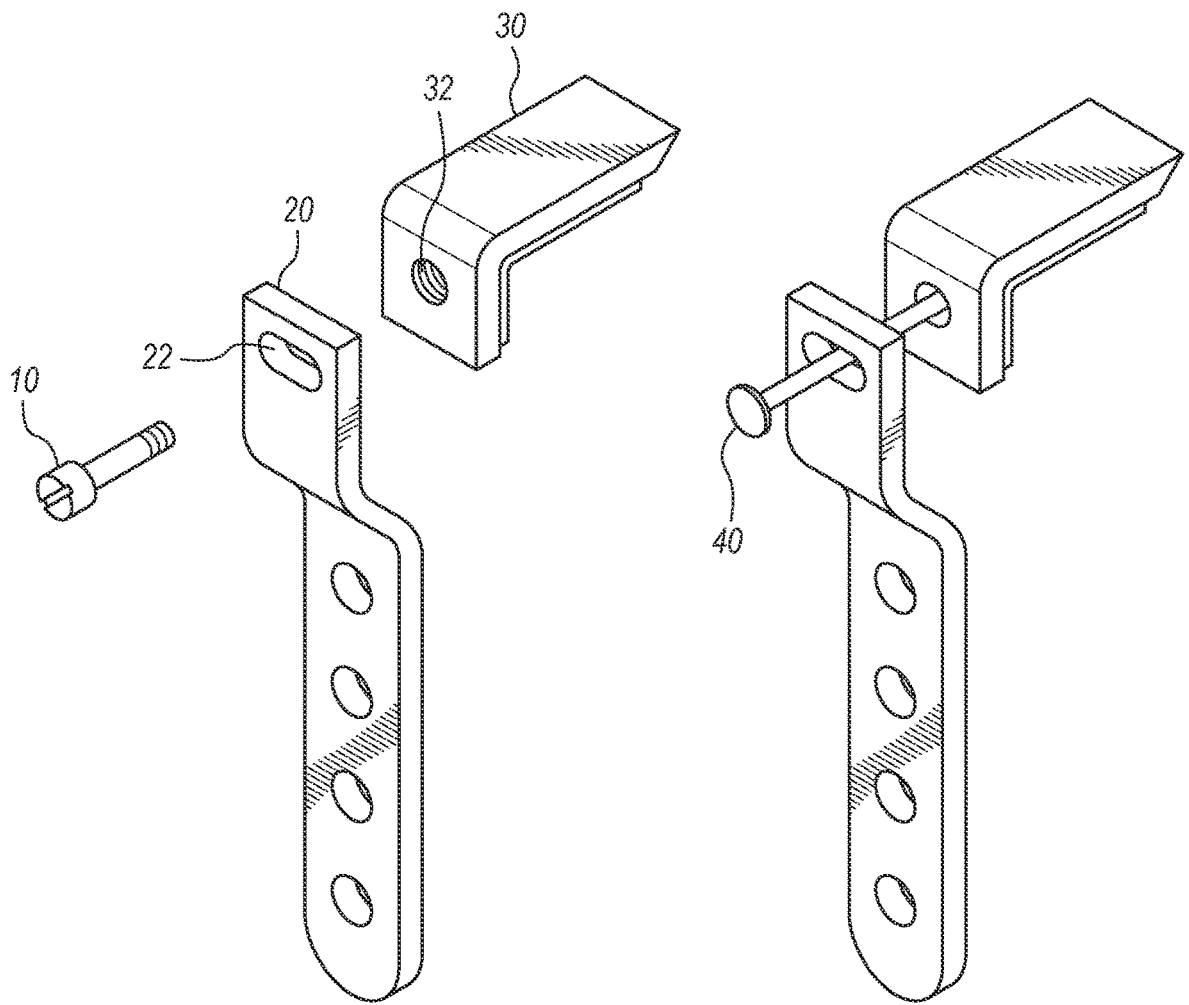
FIG. 1A  FIG. 1B
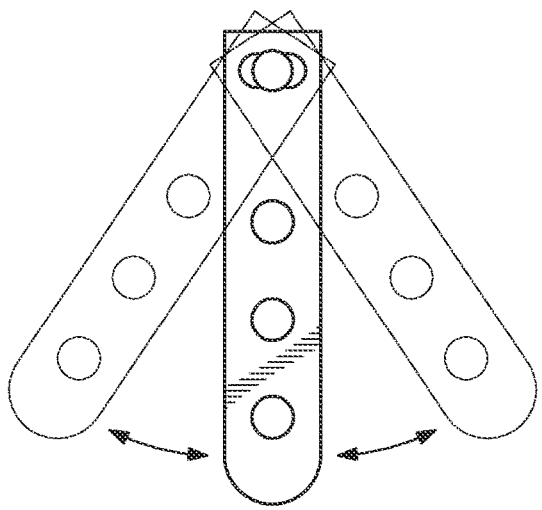
FIG. 1C

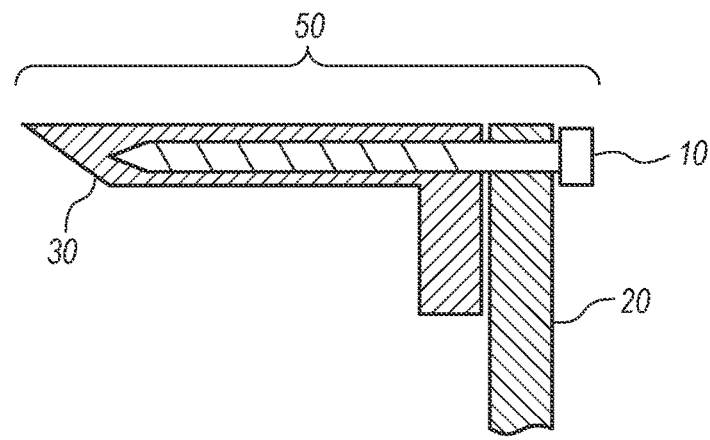
FIG. 2
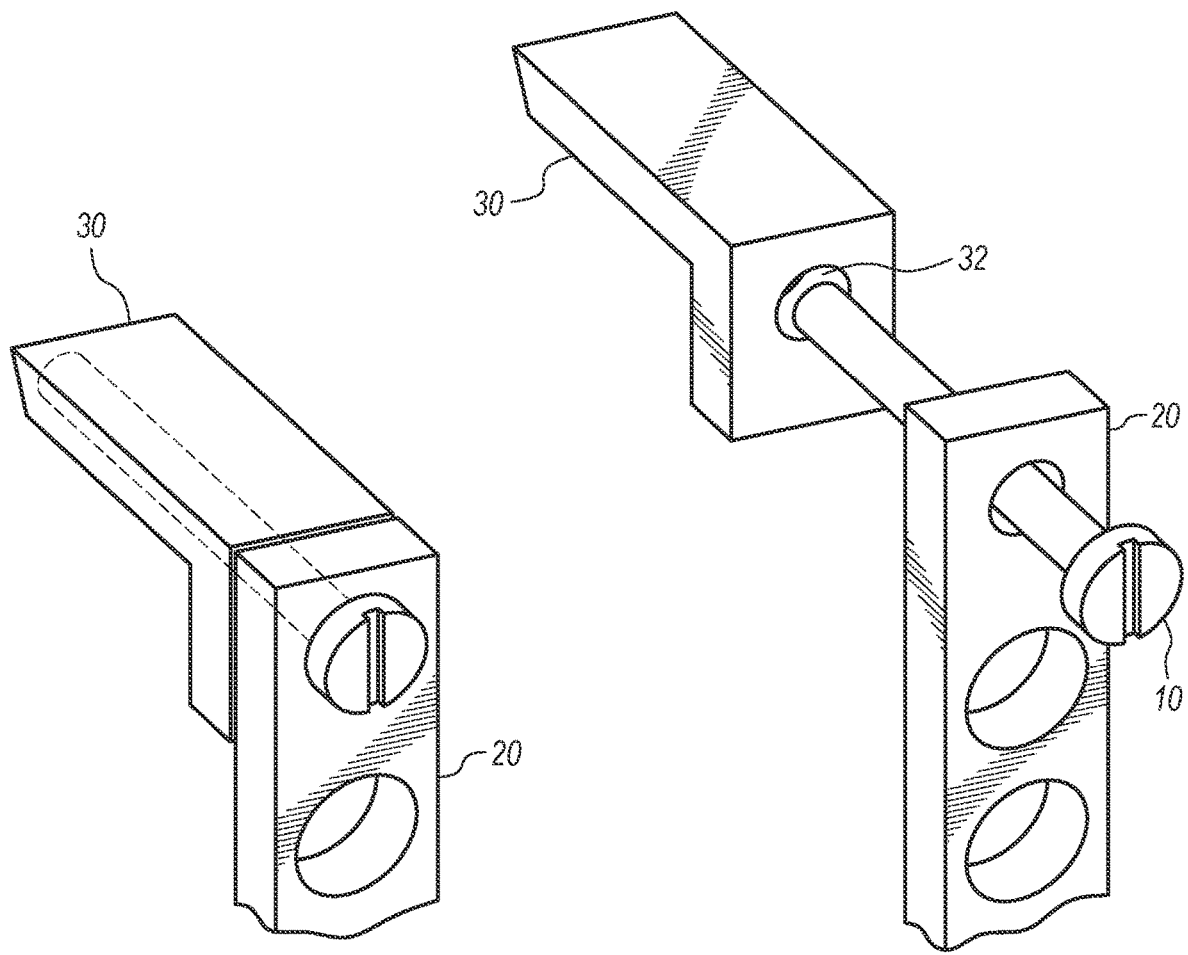
FIG. 4  FIG. 3

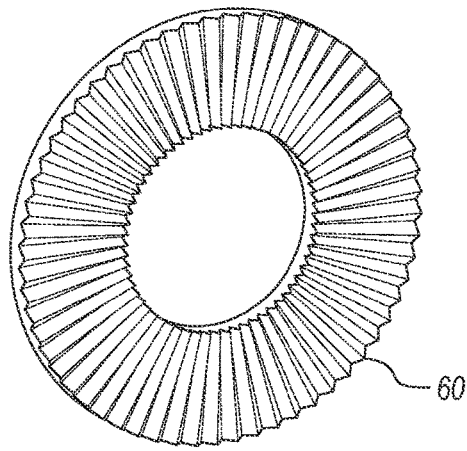
FIG. 5
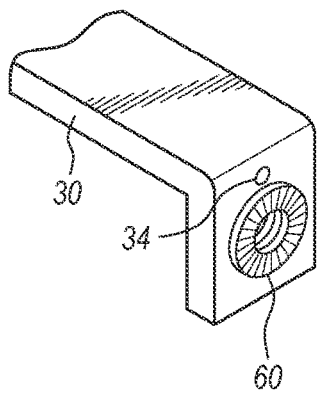
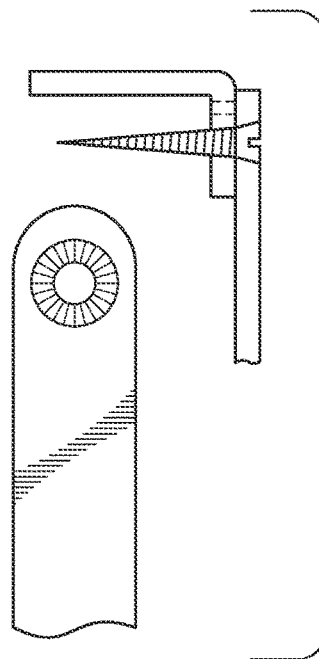
FIG. 6
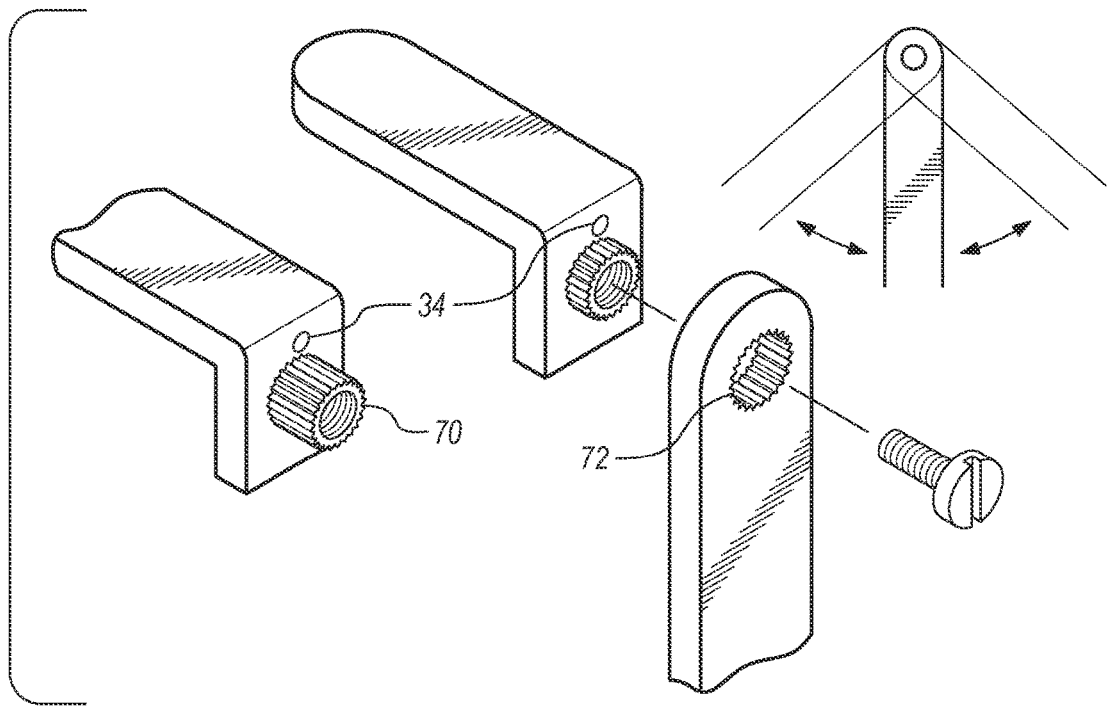
FIG. 7

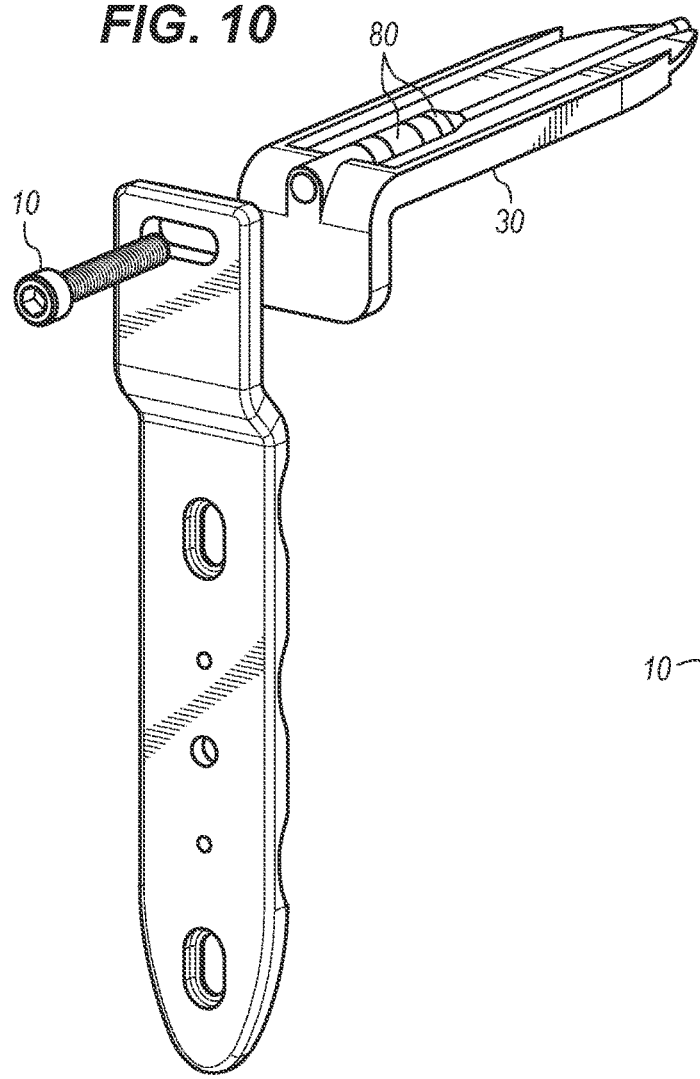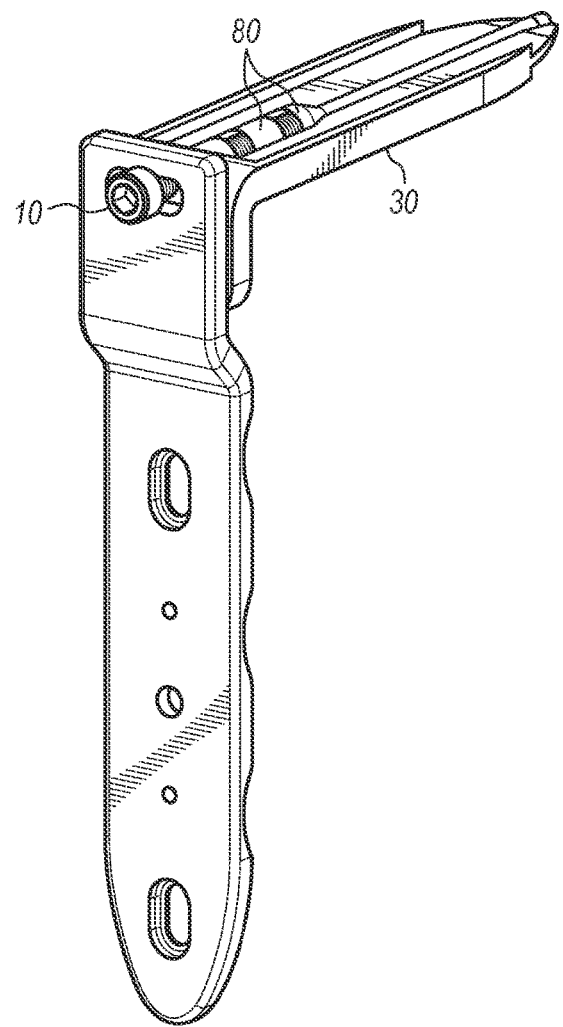

DEVICES AND METHODS FOR CORRECTION OF HIP DEFORMITIES

FIELD OF THE INVENTION

This application relates generally to the field of devices for use in the surgical correction of specific deformities, particular in children and adolescents, namely, proximal femoral deformities.

BACKGROUND OF THE INVENTION

Three-dimensional proximal femoral deformities are common and need surgical correction in patients with developmental dysplasia of the hip, slipped capital femoral epiphysis, neuromuscular hip disorders and other hip conditions in children and young adults. Proximal femoral implants that are currently available in the market work well for correction of simple coronal or sagittal plane deformities. However, they are limited in their ability to adequately address complex deformity corrections in all three planes. The primary limitations of the existing implants are: 1) there are limited options of varying configurations of plate design that require modification of the osteotomy to accommodate the existing implants; 2) no implants allow for variation of the sagittal plane of the femoral shaft in relation to the proximal fragment; 3) current implants do not allow for adequate medialization of the femoral shaft in certain cases; 4) current implants force surgeons to make the proximal femoral osteotomy more distal in the intertrochanteric region of the femur which can sometimes lead to delayed healing; 5) current implants are too rigid and do not allow for compression of the femoral osteotomy which can sometimes lead to delayed healing.

Other known techniques in the art for eliminating deformities of the proximal femur include osteotomies of various configurations in the femoral neck and fixing its osteotomized fragments to ensure their subsequent metered movement using an external fixation device until the anatomically correct contours of the proximal femur and its spatial position are restored. However, these methods are traumatic and, in most cases, result in inflammation at the sites of introduction of trans-osseous elements, such as knitting needles, rods, screws, etc. In addition, the use of these methods requires the application of a bulky external fixation apparatus, including external supports in the form of rings and half rings, which significantly reduces the patient's quality of life.

There remains a need in the art for modular fixation of the proximal and distal portions of the proximal femur after a corrective osteotomy is performed, thus allowing for precise deformity correction without being limited by the available implants.

SUMMARY OF THE INVENTION

The present invention provides an instrument for use in entering bone, comprising a blade having at least two prongs and a center cannulation to accommodate a guide wire, wherein the center-cannulated guide wire allows for precise placement of the instrument within the proximal femoral neck of an individual. Optionally, the blade is a variable blade wherein, depending on the size of the individual, the variable blade can be used to enter the proximal femoral neck with precision and obtain a rigid fixation within the bone.

In a preferred embodiment, an inserter is used and, once the blade is placed, the inserter can be removed with the outer margin of the blade placed flush with the cortical bone. A corrective osteotomy can then be performed about 1 cm distal to the blade in the metaphyseal intertrochanteric region of the proximal femur.

In another aspect, an appropriately sized plate is selected based on the individual's size and anatomy. The proximal anatomy of the plate is variable, allowing for a deformity correction required ranging from about 80 degrees to about 140 degrees, in 10-degree increments.

Preferably, the connection between the blade and appropriately sized plate allows for anterior to posterior translation of the appropriately sized plate relative to the blade using an oval aperture. This will allow for sagittal plan translation as well as flexion/extension as required during deformity correction. A screw placed through the oval aperture is fixated into the blade to lock the articulation between these two devices. Optionally, an additional locking screw is positioned to affix the plate to the proximal femur.

In another aspect, additional locking or non-locking screws are used to affix the distal femoral fragment to the plate. Oblong holes in this portion of the plate can accommodate screws to provide compression of the fracture site.

The modular configuration of the blade and blade and the oval aperture between the two devices will allow for significant flexibility during deformity correction. For example, if a proximal femoral osteotomy is performed after a surgical hip dislocation, the blade can be used to affix the greater trochanter back to the proximal femur prior to performing the intertrochanteric osteotomy. Currently available implants do not provide this option and can be prone to implant failure or nonunion.

In yet another aspect, the present invention provides for a surgical instrument assembly comprising a modular blade and a modular plate, wherein the modular blade comprises a top surface and a bottom surface, wherein the modular blade and the modular plate are attached to each other at one point of contact, wherein the modular plate is longitudinally arranged to accommodate a plurality of positions of the assembly once surgically attached. Preferably, wherein the modular blade comprises a threaded hole and the modular plate comprises an oval/elliptical feature. Preferably, the modular blade comprises a blade housing that can accommodate a set screw. Most preferably, the modular blade is connected to the modular plate via a set screw extending through the oval/elliptical feature of the modular plate and through the threaded hole of the blade housing of the modular blade. Optionally, the blade housing can accommodate a guidewire that is inserted through the oval/elliptical feature of the modular plate and through the threaded hole of the blade housing of the modular blade. Optionally, the modular blade comprises a guidewire port positioned above the threaded hole, which is aligned with a complementary guidewire port positioned above the oval/elliptical feature of the blade housing of the modular blade.

Alternatively, the surgical instrument assembly of the present invention comprises a modular blade and a modular plate, wherein each of the modular blade and the modular plate further comprise a connection port, wherein a threaded washer is embedded within the connection ports and arranged such that the modular blade and the modular plate are connected to each other via alignment of the connection ports with a set screw. Optionally, the threaded washer is a low-profile design. Alternatively, the threaded washer is a high-profile design.

In yet another aspect, the modular plate further comprises a hinge positioned under the connection port or the oval/elliptical feature. In yet another embodiment, the oval/elliptical feature comprises a plurality of cutout features along the feature's edges that articulate with the modular blade once connected and allow for flexion/extension of the modular plate in relation to the modular blade in a sagittal plane.

Alternatively, the blade housing may be partially open, allowing for exposure of the set screw to connect directly to bone once surgically inserted. In this embodiment, the partial opening of the blade housing is preferably spaced every 5 mm, with the opening extending 10 mm before the next 5 mm closure. Most preferably, the partially opened blade housing of the modular blade is open at the top surface and the bottom surface of the blade housing. Optionally, the blade housing is arranged in a fully open configuration, resulting in the total exposure of the set screw. Most preferably, the fully open blade housing configuration is open at the top surface and the bottom surface of the blade housing

BRIEF DESCRIPTION OF THE DRAWINGS

The novel features of the present invention are set forth herein embodied in the form of the claims of the invention. Features and advantages of the present invention may be best understood by reference to the following detailed description of the invention, setting forth illustrative embodiments and preferred features of the invention, as well as the accompanying drawings, of which:

FIGS. 1A-1C show two embodiments of the instrument and blade system described in the present invention. FIG. 1A shows the system having an oval/elliptical hole in the plate utilized without a guidewire and only a set screw; FIG. 1B shows the system having an oval/elliptical hole in the plate utilized with a guidewire; FIG. 1C shows range of motion for the plate element (with blade portion being fixed) of the preferred system of the present invention.

FIG. 2 shows a side view of the set screw in locked position and connecting the plate feature directly to the blade feature of the preferred system of the present invention.

FIG. 3 shows how the set screw is initially used to bring together (before locking) the plate feature (having a threaded portion) and the blade feature.

FIG. 4 is a perspective view of the set screw in locked position and the screw as positioned within the blade after locking.

FIG. 5 shows alternative embodiments of certain elements within the present invention, including a low-profile design of the washer for use in the present invention FIG. 6 shows the low-profile embodiment of the washer as installed in the plate and the blade.

FIG. 7 shows the high-profile embodiment of the washer as installed in the plate and the blade, as well as the available range of motion resulting therefrom.

FIG. 10 shows a top perspective view of the blade housing and the openings spaced accordingly to allow the screw to contact the bone during insertion prior to assembly.

FIG. 11 shows the assembled system with the screw exposed at the appropriate spacings within the blade housing.

DETAILED DESCRIPTION OF THE INVENTION

Definitions

Figure 8:
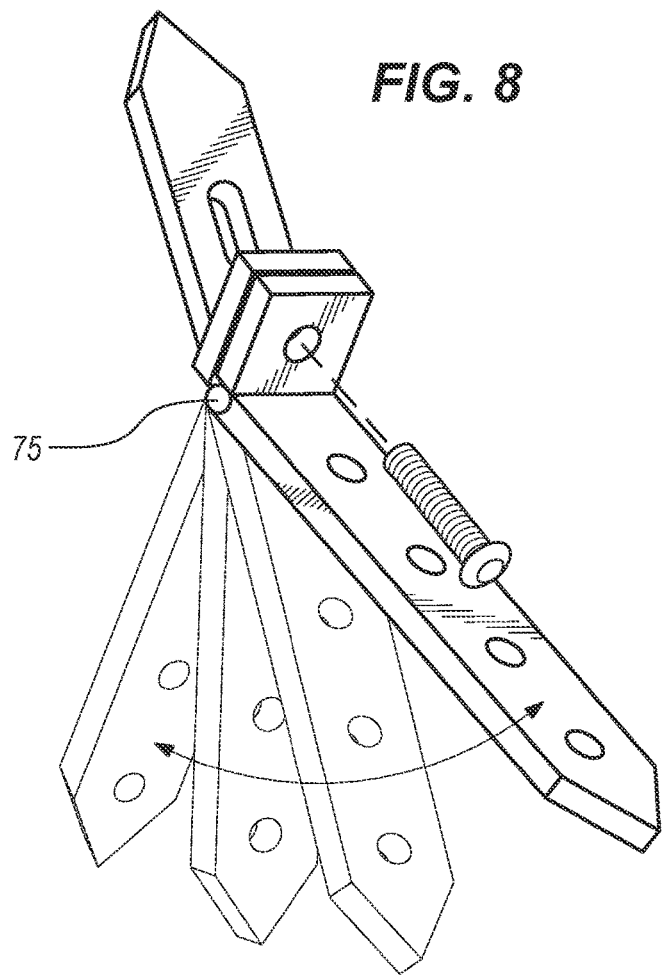
FIG. 8 illustrates a hinge element allowing for extended range of motion for adjustments to the plate prior to surgical installation.

The present invention provides for a system for use in the treatment of certain orthopedic conditions, including those related to the surgical correction of specific deformities, particular in children and adolescents, namely, proximal femoral deformities. The following description of various embodiments is merely exemplary in nature and is in no way intended to limit the invention, its application, or uses. Although the following description relates generally to the surgical correction of specific deformities including proximal femoral deformities, it will be understood that the systems and methods may be used for other appropriate surgical corrections.

Novel features of the present invention include at least the following improvements over the state of the art in the field:
1. An insertion blade is placed over a guide wire and retained in the proximal femur to simplify implant insertion.
2. The insertion blade can be forked with 2 prongs for use in infants, have a narrowing tip for use in children or "T" shaped for use in adolescents and adults.
3. The insertion blade has a 20 mm cut out to allow for insertion of a locking screw into the adjacent bone.
4. Side plate attaching to femoral shaft is modular with various configurations allowing for varus and valgus correction (ranging from 90 degrees to 150 degrees at 10 degree increments) as well as varying degrees of medialization of the femoral shaft (ranging from 0 to 20 mm at 10 mm increments) in the coronal plane.
5. Attachment interface between insertion blade and side plate includes an oblong hole that allows anterior to posterior translation of the side plate in relation to the blade in the sagittal plane.
6. Attachment interface between insertion chisel and side plate includes a locking toothed circular articulation that allows for rigid fixation of flexion and extension of the side plate in relation to the blade in the sagittal plane.

With reference to FIG. 1, an orthopedic instrument system is illustrated. In one particular embodiment, the present invention provides for plate 20 being connected to blade 30 with set screw 10 (FIG. 1A). Blade 30 has a threaded hole 32 that aligns with elliptical shaped feature 22 on plate 20. In this embodiment, there is no guidewire and set screw 10 is utilized to connect plate 20 with blade 30 through the threaded features on blade 30 once aligned with elliptical shaped feature 22 on plate 20.

In an alternative embodiment, plate 20 is connected to blade 30 using guidewire 40 to align the hole in blade 30 with elliptical shaped feature 22 on plate 20 (FIG. 1B). In this embodiment, guidewire 40 extends through elliptical shaped feature 22 on plate 20 to properly align with blade 30. Preferably, the system provides for blade 30 to be in a fixed position with plate 20 having a rotational motion with several degrees of freedom in order to meet with misaligned bone at the surgical site (FIG. 1C).

With reference to FIG. 2, a detailed, cross-sectional side view of the orthopedic system 50 of the present invention is provided. As shown, there are tight junctions between plate 20 and blade 30 once set screw 10 is fully engaged.

FIG. 3 shows a perspective view of the positioning of the elements prior to blade 30 forming a tight connection with plate 20 by way of set screw 10. In this embodiment, blade 30 has threaded hole 32 to accommodate set screw 10. FIG. 4 shows the resulting attached system of set screw 10 bringing blade 30 into the tight connection with plate 20.

The present invention further provides alternative preferred embodiments of locking washer systems, wherein these washer systems may be machined features of the instrument or they may be additional separate features. FIG. 5 shows a low-profile washer element 60 as used within the present invention. Low-profile washer element 60 is embedded within plate 20 and blade 30 in order to provide a tighter junction after set screw 10 is fixed (FIG. 6). Optionally, guidewire port 34 may be used to provide accurate alignment within this embodiment.

Low-profile washer element 60 is appropriately machined from, preferably, steel in order to provide necessary grip strength at the site, which will hold, in fixed fashion, any adjustable/predetermined angle between plate 20 and blade 30. Once the proper angle is established, set screw 10 is applied in order to provide a final lock to the system.

As shown at FIG. 7, high-profile washer element 70 may be used in certain conditions. High-profile washer element 70 is used to provide a more aggressive gripping feature at the plate 20/blade 30 junction. Preferably, high-profile washer element 70 is located on blade 30 and intersects with high-profile counter washer element 72 located within plate 20 to allow for multiple angle adjustment once blade 30 is attached to plate 20. Guidewire port 34 may be used to provide accurate alignment within this embodiment. A greater range of angles can be achieved within this embodiment. Once the proper angle is established, set screw 10 is applied in order to provide a final lock to the system.

An alternative embodiment to the present invention is shown at FIG. 8, which shows articulating hinge 75 in plate 20 above the first hole which locks plate 20 with blade 30. Hinge 75 allows for about 60 total degrees of articulation in the coronal plane, ranging from about −30 to about 30 degrees.

Figure 9:
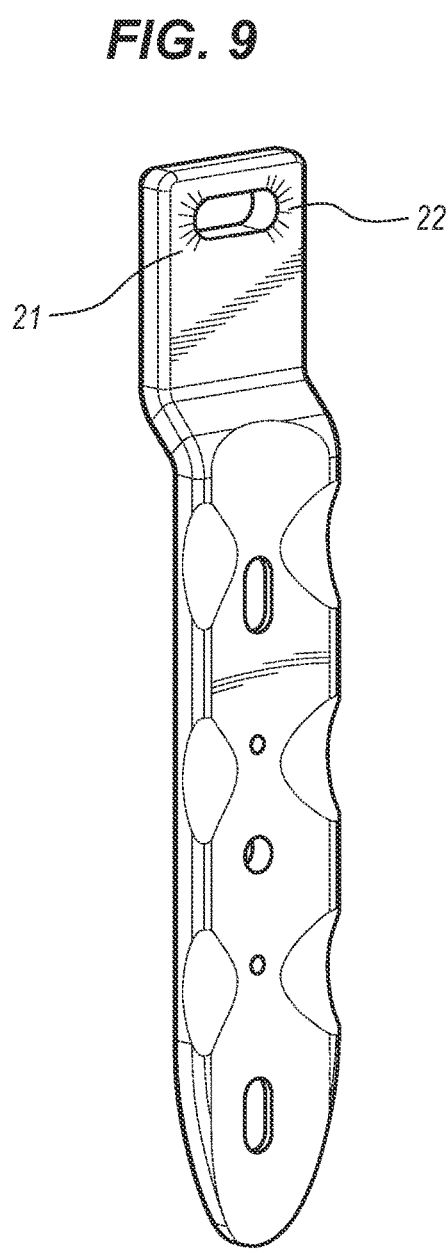
FIG. 9 shows an oval or elliptical shaped hole feature as the proximal attachment point between the blade and the femoral side plate, as well as specific topography of internal plate structure.

FIG. 9 shows elliptical shaped feature 22 as the proximal attachment point between the chisel and the femoral side plate. Elliptical shaped feature 22 allows for anterior/posterior translation of plate 20. Elliptical shaped feature 22 further comprises cutout features 21 along the edges that articulate with blade 30 and allow for flexion/extension of plate 20 in relation to blade 30 in a sagittal plane.

FIG. 10 shows a top perspective view of the blade 30 prior to screw assembly, demonstrating blade housing 80 is solid in the first approximately 5 mm, then open for the following approximately 10 mm, in order to allow set screw 10 to enable purchase into the proximal femoral bone. FIG. 11 shows the assembled system and how set screw 10 is exposed within blade housing 80 once set screw 10 is fully engaged.

Figure 12:
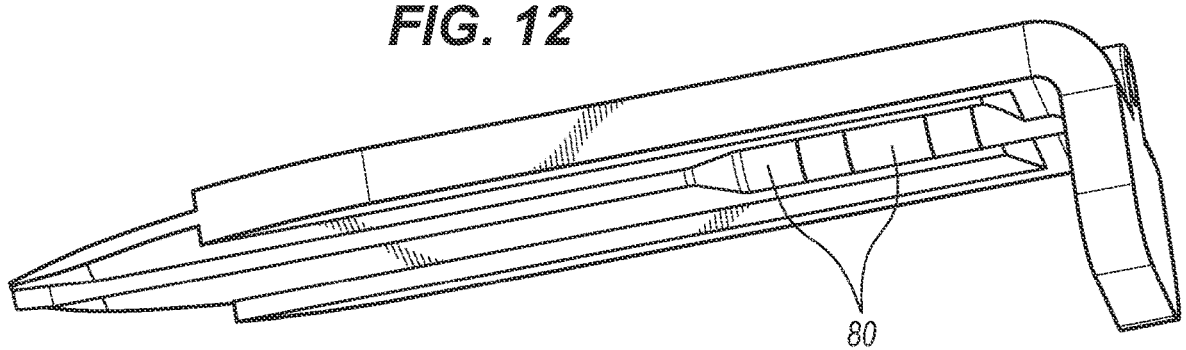
FIG. 12 shows an underside, perspective view of the blade housing being arranged in accordance with the topside features described in FIGS. 10-11.

FIG. 12 shows an underside, perspective view of blade 30 with blade housing 80 also being arranged in accordance with the topside features described in FIGS. 10-11.

Figure 13:
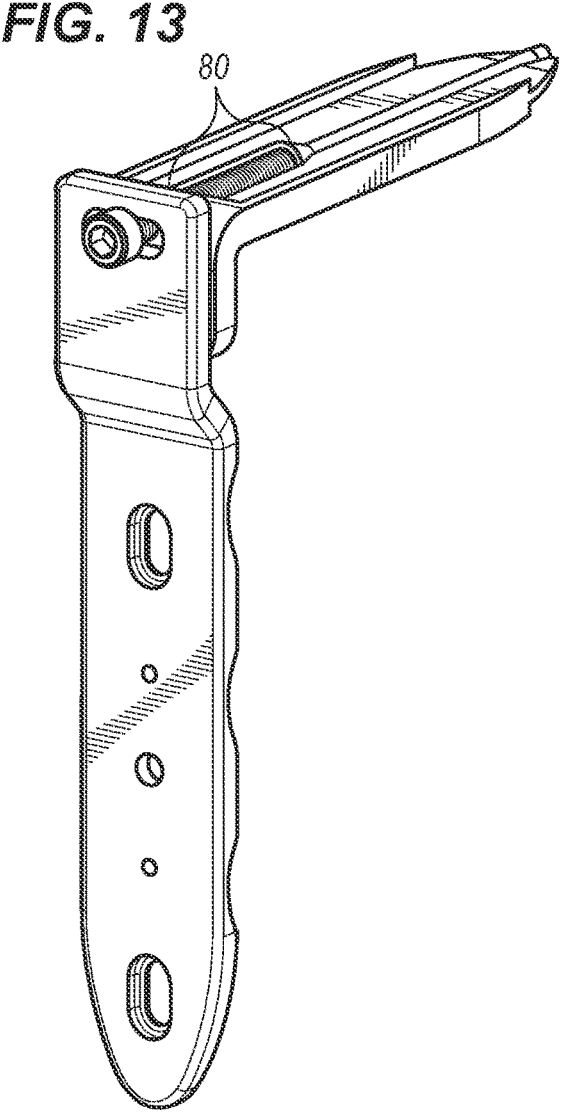
FIG. 13 shows an alternative embodiment to the full length of the blade housing being open in form, with the set screw being exposed through the blade housing length.
Figure 14:
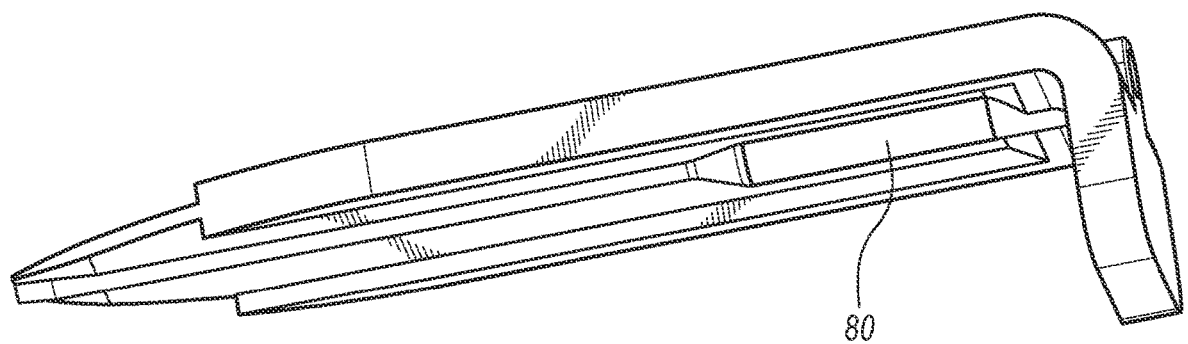
FIG. 14 shows an underside, perspective view of the full length opening of the blade housing from the blade shown in FIG. 13.

FIG. 13 shows an alternative embodiment to blade 30, wherein blade housing 80 is completely open along its length, thereby allowing set screw 10 to be fully exposed along such length. An underside, perspective view of the fully open version of blade housing 80 is illustrated in FIG. 14. This embodiment shows the opening of blade housing 80 being in continuous form, exposing the threads of set screw 10 to the surrounding bone throughout the length of the opening.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. As used in this specification and in the appended claims, the singular forms include the plural forms. For example, the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

We claim:

1. A surgical instrument assembly comprising a modular blade and a modular plate, wherein the modular blade comprises a top surface and a bottom surface, wherein the modular blade and the modular plate are configured to be attached to each other, wherein the modular plate is longitudinally arranged to accommodate a plurality of relative positions of the modular plate to a bone once surgically attached, wherein the modular blade comprises a blade housing that can accommodate a set screw, further wherein the blade housing is arranged to allow the set screw to enable purchase into the bone, wherein the blade housing is configured to be perpendicular to the modular plate and configured in a partially open configuration to allow exposure of the set screw to connect directly to the bone once surgically inserted, wherein the partially open configuration of the blade housing comprises at least one opening and at least one closure, wherein the at least one opening extends about 10 mm and the at least one closure extends about 5 mm.

2. The surgical instrument assembly of claim 1, wherein the blade housing comprises a threaded hole and the modular plate comprises an oval/elliptical feature.

3. The surgical instrument assembly of claim 2, wherein the modular blade is connected to the modular plate via the set screw extending through the oval/elliptical feature of the modular plate and the threaded hole of the blade housing.

4. The surgical instrument assembly of claim 2, wherein the blade housing can accommodate a guidewire that is inserted through the oval/elliptical feature of the modular plate and through the threaded hole of the blade housing of the modular blade.

5. The surgical instrument assembly of claim 2, wherein each of the modular blade and the modular plate further comprise a connection port, wherein a threaded washer is embedded within the connection ports and arranged such that the modular blade and the modular plate are configured to be connected to each other via alignment of the connection ports with a set screw.

6. The surgical instrument assembly of claim 5, wherein the threaded washer is a low-profile design such that the threaded washer is flush with respect to the modular plate when inserted.

7. The surgical instrument assembly of claim 5, wherein the threaded washer is a high-profile design such that the threaded washer, when inserted within the modular blade, protrudes outward to align with a counter washer element within the modular plate to allow for multiple angle adjustments once the modular blade is attached to the modular plate.

8. The surgical instrument assembly of claim 5, wherein the modular plate further comprises a hinge positioned below the connection ports or the oval/elliptical feature.

9. The surgical instrument assembly of claim 8, wherein the oval/elliptical feature comprises a plurality of cutout features along the feature's edges that articulate with the modular blade once connected and allow for flexion/extension of the modular plate in relation to the modular blade in a sagittal plane.

* * * * *